United States Patent
Okada et al.

(10) Patent No.: US 10,172,307 B2
(45) Date of Patent: Jan. 8, 2019

(54) PLANT-ADVENTITIOUS-EMBRYO INDUCTION METHOD, PLANT RESTORATION METHOD, AND PLANT REPRODUCTION METHOD

(71) Applicant: SUMITOMO RUBBER INDUSTRIES, LTD., Kobe-shi, Hyogo (JP)

(72) Inventors: Akari Okada, Kobe (JP); Yukino Inoue, Kobe (JP); Satoshi Kuroda, Kobe (JP)

(73) Assignee: SUMITOMO RUBBER INDUSTRIES, LTD., Kobe-shi, Hyogo (JP)

( * ) Notice: Subject to any disclaimer, the term of this patent is extended or adjusted under 35 U.S.C. 154(b) by 306 days.

(21) Appl. No.: 14/422,339

(22) PCT Filed: Sep. 4, 2013

(86) PCT No.: PCT/JP2013/073740
§ 371 (c)(1),
(2) Date: Feb. 18, 2015

(87) PCT Pub. No.: WO2014/038564
PCT Pub. Date: Mar. 13, 2014

(65) Prior Publication Data
US 2015/0223420 A1 Aug. 13, 2015

(30) Foreign Application Priority Data
Sep. 5, 2012 (JP) ................................ 2012-194867

(51) Int. Cl.
*A01H 4/00* (2006.01)
*A01H 6/14* (2018.01)
*C12N 5/04* (2006.01)

(52) U.S. Cl.
CPC ............. *A01H 4/005* (2013.01); *A01H 4/001* (2013.01); *A01H 4/008* (2013.01); *A01H 6/14* (2018.05); *C12N 5/04* (2013.01); *C12N 2500/76* (2013.01)

(58) Field of Classification Search
None
See application file for complete search history.

(56) References Cited

U.S. PATENT DOCUMENTS

2004/0210958 A1* 10/2004 Duncan ............... A01H 4/005
800/278
2005/0022267 A1* 1/2005 Ryu .................... C12N 15/8205
800/294

FOREIGN PATENT DOCUMENTS

JP 2005-130815 A 5/2005
WO WO 2012/099100 A1 7/2012

OTHER PUBLICATIONS

Jayasree et al (1999. Somatic embryogenesis and plant regeneration from immature anthers of Hevea brasiliensis (Muell.) Arg. Current Science).*
Dunlap, J.R. and H Clemens (eds.). 1919. Rubber-Producing Weeds in Germany in the India Rubber World, vols. 59-60, p. 201.*
Hutchinson et al. The biology of Canadian weeds. 63. *Sonchus asper* (L.) Hill and *S. oleraceus* L. Can J. Plant Sci. 64: 731-744.*
Buchanan et al. 1978. Hydrocarbon- and rubber-producing crops. Economic Botany 32: 131-145.*
Dhar et al. 1989. In vitro propagation of guayule (*Parthenium argentatum*)—a rubber yielding shrub.*
Carron M.P. et al., "Hevea micropropagation by somatic embryogenesis", Plantations, recherche, développement, May-Jun. 1998, vol. 5, No. 3, pp. 187-194, with English translation.
Jayasree et al., "Somatic embryogenesis and plant regeneration from immature anthers of Hevea brasiliensis (Muell.) Arg.", Current Science, vol. 76, No. 9, May 10, 1999, pp. 1242-1245.

* cited by examiner

*Primary Examiner* — Ashley K Buran
*Assistant Examiner* — Karen M Redden
(74) *Attorney, Agent, or Firm* — Birch, Stewart, Kolasch & Birch, LLP

(57) ABSTRACT

The present invention provides a method of regenerating a plant, which allows stable regeneration of plants from calli; and a method of reproducing a plant, which allows stable reproduction of plants without being affected by weather, seasons or other factors. The present invention relates to a method of regenerating a plant, including a step of inducing adventitious embryos from calli; and a method of reproducing a plant, including a step of inducing adventitious embryos from calli.

14 Claims, 1 Drawing Sheet

(a) Adventitious embryo formation
(b) Shoot formation
(c) Shoot elongation
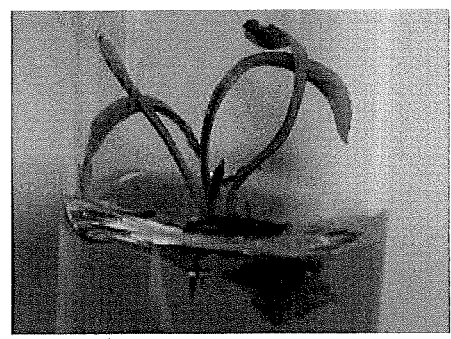
(d) Rooting

PLANT-ADVENTITIOUS-EMBRYO INDUCTION METHOD, PLANT RESTORATION METHOD, AND PLANT REPRODUCTION METHOD

TECHNICAL FIELD

The present invention relates to a method of inducing adventitious embryos of a plant, a method of regenerating a plant, and a method of reproducing a plant.

BACKGROUND ART

Currently, natural rubber (one example of polyisoprenoids) for use in industrial rubber products is produced by growing rubber-producing plants, such as *Hevea brasiliensis* of the family Euphorbiaceae or *Ficus elastica* of the family Moraceae, biosynthesizing natural rubber in the laticifer cells of the plants, and extracting the natural rubber from the plants by hand.

At present, *Hevea brasiliensis* is practically the only one source of natural rubber for industrial use. It is also widely used in large quantities in various applications as a main raw material of rubber products. Unfortunately, *Hevea brasiliensis* is a plant that grows only in limited areas such as in Southeast Asia and South America. Moreover, *Hevea brasiliensis* requires about seven years from the time it is planted until it matures enough to allow rubber extraction. Furthermore, the seasons for extracting rubber from it are limited in some cases. Additionally, the period during which natural rubber can be extracted from the mature trees is limited to 20 to 30 years.

Although more natural rubber is expected to be needed, in particular, by developing countries in years to come, for the reason mentioned above it is difficult to greatly increase the production of natural rubber using *Hevea brasiliensis*. Depletion of natural rubber sources is therefore of concern and there are needs for stable natural rubber sources other than mature *Hevea brasiliensis* and for improvement in productivity of natural rubber from *Hevea brasiliensis*.

Under such circumstances, natural rubber sources other than *Hevea brasiliensis* are being actively sought. At least 2000 types of isoprenoid-producing plants other than *Hevea brasiliensis* have been known. In particular, Guayule and *Taraxacum koksaghyz* are being studied as novel natural rubber sources. Some plants of the family Asteraceae are also known to produce isoprenoids. One example is *Sonchus oleraceus* which naturally grows in a wide range of areas in Japan.

If these plants are used as novel natural rubber sources, mass reproduction of these plants will be required for mass production of natural rubber. Plants may be reproduced in large quantities, for example, by a method of growing plants from seeds or a method of reproducing plants from cuttings. These methods, however, can easily be affected by weather, seasons or other factors and thus may fail to stably reproduce plants.

There are also attempts to increase the production of natural rubber using *Hevea brasiliensis*. *Hevea brasiliensis* plantlets can be reproduced by sowing and growing seeds into seedlings, raising the seedlings to prepare rootstocks, and grafting buds formed on clean plantlets to the rootstocks. The number of buds obtainable from plant clones is limited. Thus, to widely introduce superior varieties, these superior varieties of clean plantlets need to be reproduced in large quantities.

Moreover, grafting, which is a conventional clean reproduction technique, may, at the same time, allow inheritance of diseases derived from the original trees and thus may result in reproduction of plantlets suffering from the diseases. Accordingly, there is a need for methods of stably reproducing plants.

Meanwhile, a possible approach to increase the production of isoprenoids in plants is to modify plants so as, for example, to enhance stress resistance or increase the amount of isoprenoids accumulated in the plant. Plants may also be modified using artificial crossing or by mutation; however, such methods have difficulty in efficiently providing the plants with desired characteristics and thus have low feasibility. Therefore, it is considered that plants should be modified using cell technologies in which a target gene is introduced into plant cells to provide a desired characteristic.

If cell technologies are used, plant cells into which a target gene is introduced need to be redifferentiated into plants. In other words, the plant cells (e.g. calli) need to be regenerated into plants. Unfortunately, although various tissue culture studies have been made on plants, there are few studies suggesting how to regenerate plants from calli of isoprenoid-producing plants. Thus, it has been difficult to stably regenerate plants from calli.

SUMMARY OF INVENTION

Technical Problem

The present invention aims to solve the above problems and provide a method of regenerating a plant, which allows stable regeneration of plants from calli; and a method of reproducing a plant, which allows stable reproduction of plants without being affected by weather, seasons or other factors. The present invention also aims to provide a method of inducing adventitious embryos of a plant.

Solution to Problem

The inventors of the present invention conducted intensive studies and thereby found that by inducing adventitious embryos from calli, shoots can then be stably formed and the formed shoots can be elongated and rooted. In other words, the inventors found that by inducing adventitious embryos from calli, it is possible to stably regenerate plants from the calli and to stably reproduce the plants, and thus completed the present invention. Specifically, the present invention relates to a method of regenerating a plant, including a step of inducing adventitious embryos from calli.

In the regeneration method, the adventitious embryo induction is preferably followed by forming shoots.

The regeneration method preferably includes a regeneration induction step of culturing the calli in a regeneration induction medium that contains a plant growth hormone and a carbon source to form the adventitious embryos and shoots; and a rooting step of culturing the shoots in a rooting medium to root the shoots.

The regeneration method preferably includes a regeneration induction step of culturing the calli in a regeneration induction medium that contains a plant growth hormone and a carbon source to form the adventitious embryos and shoots; an elongation step of culturing the formed shoots in an elongation medium to elongate the shoots; and a rooting step of culturing the elongated shoots in a rooting medium to root the shoots.

In a preferred embodiment of the regeneration method, particularly in the case of using a plant of the family Asteraceae (preferably a plant of the genus *Sonchus*, and especially *Sonchus oleraceus*), the elongation medium and the rooting medium are free of plant growth hormones.

In the regeneration method, the plant is preferably an isoprenoid-producing plant, more preferably a plant of the family Asteraceae or the family Euphorbiaceae, still more preferably a plant of the genus *Sonchus* or the genus *Hevea*, and particularly preferably *Sonchus oleraceus* or *Hevea brasiliensis*.

The present invention relates to a method of reproducing a plant, including a step of inducing adventitious embryos from calli.

The reproduction method preferably includes a step of inducing the calli from tissue sections of the plant.

In the reproduction method, the adventitious embryo induction is preferably followed by forming shoots.

The reproduction method preferably includes an induction step of culturing tissue sections of the plant in an induction medium that contains a plant growth hormone and a carbon source to induce the calli; a regeneration induction step of culturing the calli in a regeneration induction medium that contains a plant growth hormone and a carbon source to form the adventitious embryos and shoots; and a rooting step of culturing the shoots in a rooting medium to root the shoots.

The reproduction method preferably includes an induction step of culturing tissue sections of the plant in an induction medium that contains a plant growth hormone and a carbon source to induce the calli; a regeneration induction step of culturing the calli in a regeneration induction medium that contains a plant growth hormone and a carbon source to form the adventitious embryos and shoots; an elongation step of culturing the formed shoots in an elongation medium to elongate the shoots; and a rooting step of culturing the elongated shoots in a rooting medium to root the shoots.

In a preferred embodiment of the reproduction method, particularly in the case of using a plant of the family Asteraceae (preferably a plant of the genus *Sonchus*, and especially *Sonchus oleraceus*), the elongation medium and the rooting medium are free of plant growth hormones.

In the reproduction method, the plant is preferably an isoprenoid-producing plant, more preferably a plant of the family Asteraceae or the family Euphorbiaceae, still more preferably a plant of the genus *Sonchus* or the genus *Hevea*, and particularly preferably *Sonchus oleraceus* or *Hevea brasiliensis*.

The present invention relates to a method of inducing adventitious embryos, including culturing calli in a medium that contains a plant growth hormone and a carbon source to induce the adventitious embryos.

In the method of inducing adventitious embryos, preferably, the medium has a solidifying agent concentration of 0.1 to 2% by mass, an auxin plant hormone concentration of $1 \times 10^{-3}$ to 15 mg/L, a cytokinin plant hormone concentration of $1 \times 10^{-3}$ to 15 mg/L, and a sucrose concentration of 1 to 5% by mass, and a culture temperature is 0° C. to 40° C.

Advantageous Effects of Invention

Since the method of regenerating a plant of the present invention includes a step of inducing adventitious embryos from calli, it allows stable regeneration of plants from calli. Moreover, since the method of reproducing a plant of the present invention includes a step of inducing adventitious embryos from calli, plants can be stably reproduced, without being affected by weather, seasons or other factors, by tissue culture under a controlled environment. Furthermore, since the method of inducing adventitious embryos of the present invention includes culturing calli in a medium that contains a plant growth hormone and a carbon source to induce the adventitious embryos, it suitably allows adventitious embryo induction.

BRIEF DESCRIPTION OF DRAWINGS

FIG. 1 shows photographs illustrating adventitious embryo formation, shoot formation, shoot elongation, and rooting of *Sonchus oleraceus*.

DESCRIPTION OF EMBODIMENTS

The method of inducing adventitious embryos of the present invention includes culturing calli in a medium that contains a plant growth hormone and a carbon source to induce the adventitious embryos. This method allows induction of adventitious embryos from calli (see FIG. 1 (*a*)).

The method of regenerating a plant of the present invention includes a step of inducing adventitious embryos from calli. By inducing adventitious embryos from calli (see FIG. 1 (*a*)) as mentioned above, followed by culturing the adventitious embryos, shoots can then be stably formed (see FIG. 1 (*b*)) and the formed shoots can be elongated (see FIG. 1 (*c*)) and rooted (see FIG. 1 (*d*)), whereby the calli can be stably regenerated into plants.

Moreover, the method of reproducing a plant of the present invention includes a step of inducing adventitious embryos from calli. Since the method of reproducing a plant of the present invention uses the above-mentioned method of regenerating a plant of the present invention, it allows stable reproduction of plants. Thus, by tissue culture under a controlled environment, plants can be stably reproduced without being affected by weather, seasons or other factors. Specifically, plants can be stably reproduced in large quantities by inducing calli from tissue sections abundantly available from plants (e.g., plant leaves and stems) and then regenerating plants from the calli by means of the method of regenerating a plant of the present invention.

Moreover, the regenerated plants are less likely to mutate compared to when the callus state is maintained (subcultured), and thus can be stably supplied. Furthermore, the regenerated plants can be grown in the soil and thus, unlike plant cells such as callus, there is no need for expensive plant growth regulators to maintain cells, which can reduce the cost.

The callus herein means undifferentiated plant cells or a mass of undifferentiated plant cells. The adventitious embryo herein means an embryo-like tissue induced from callus. The shoot herein means leaves or a juvenile plant.

The methods of the present invention (the method of regenerating a plant, the method of reproducing a plant) can be applied to any plant, but isoprenoid-producing plants are preferred because they are usable as natural rubber sources.

The isoprenoid-producing plant may be any plant capable of producing isoprenoids. Examples thereof include the genus *Hevea*, including *Hevea brasiliensis*; the genus *Sonchus*, including *Sonchus oleraceus*, *Sonchus asper*, *Sonchus brachyotus*, and *Sonchus arvensis*; the genus *Solidago*, including *Solidago altissima*, *Solidago virgaurea* subsp. *asiatica*, *Solidago virgaurea* subsp. *leipcarpa*, *Solidago virgaurea* subsp. *leipcarpa f. paludosa*, *Solidago virgaurea* subsp. *gigantea*, and *Solidago gigantea* Ait. var. *leiophylla* Fernald; the genus *Helianthus*, including *Helianthus annuus*, *Helianthus argophyllus*, *Helianthus atrorubens*,

*Helianthus debilis*, *Helianthus decapetalus*, and *Helianthus giganteus*; the genus *Taraxacum*, including *taraxacum*, *Taraxacum venustum* H. Koidz, *Taraxacum hondoense* Nakai, *Taraxacum platycarpum* Dahlst, *Taraxacum japonicum*, *Taraxacum officinale* Weber, and *Taraxacum koksaghyz*; the genus *Ficus*, including *Ficus carica*, *Ficus elastica*, *Ficus pumila* L., *Ficus erecta* Thumb., *Ficus ampelas* Burm. f., *Ficus benguetensis* Merr., *Ficus irisana* Elm., *Ficus microcarpa* L.f., *Ficus septica* Burm. f., and *Ficus benghalensis*; Guayule (*Parhenium argentatum*); and lettuce (*Lactuca serriola*). Preferred among these are plants of the family Asteraceae, such as plants of the genera *Sonchus*, *Solidago*, *Helianthus*, and *Taraxacum*; and plants of the family Euphorbiaceae, such as plants of the genus *Hevea*. More preferred are plants of the genera *Sonchus* and *Hevea*. Still more preferred are *Sonchus oleraceus* and *Hevea brasiliensis*.

The area in which *Hevea brasiliensis* grows is limited to Southeast Asia and South America. In contrast, *Sonchus oleraceus* naturally grows around the world, including European countries and Asia (e.g. Japan) and thus can be widely cultivated without limiting the production area. Moreover, *Hevea brasiliensis* requires about seven years from the time it is planted until rubber extraction, whereas *Sonchus oleraceus*, which is an annual grass, advantageously more rapidly grows.

In the following, the method of reproducing a plant of the present invention will be specifically described. Since the method of reproducing a plant of the present invention basically uses the method of inducing adventitious embryos of the present invention and the method of regenerating a plant of the present invention, the description of the method of reproducing a plant of the present invention includes the descriptions of the method of inducing adventitious embryos of the present invention and the method of regenerating a plant of the present invention.

The method of reproducing a plant of the present invention includes a step of inducing adventitious embryos from calli. Specifically, plants may be reproduced by inducing adventitious embryos from calli, and culturing the adventitious embryos to regenerate plants from the calli. More specifically, plants may be reproduced by inducing adventitious embryos from calli, culturing the adventitious embryos to form shoots, and culturing the shoots to regenerate plants from the calli.

The calli are preferably induced from tissue sections of a plant before use because calli can be stably produced. In other words, the method of reproducing a plant of the present invention preferably includes a step of inducing calli from tissue sections of a plant and a step of inducing adventitious embryos from the calli.

Specifically, the method of reproducing a plant of the present invention preferably includes an induction step of culturing tissue sections of a plant in an induction medium that contains a plant growth hormone and a carbon source to induce calli; a regeneration induction step of culturing the calli in a regeneration induction medium that contains a plant growth hormone and a carbon source to form adventitious embryos and shoots; and a rooting step of culturing the shoots in a rooting medium to root the shoots. More preferably, the method includes an induction step of culturing tissue sections of a plant in an induction medium that contains a plant growth hormone and a carbon source to induce calli; a regeneration induction step of culturing the calli in a regeneration induction medium that contains a plant growth hormone and a carbon source to form adventitious embryos and shoots; and an elongation step of culturing the formed shoots in an elongation medium to elongate the shoots; and a rooting step of culturing the elongated shoots in a rooting medium to root the shoots. In other words, the method of regenerating a plant of the present invention preferably includes the regeneration induction step and the rooting step, and more preferably includes the regeneration induction step, the elongation step, and the rooting step.

These steps will be described in the following.

(Induction Step)

In the induction step, calli are inducted, for example, by culturing tissue sections of a plant in an induction medium that contains a plant growth hormone and a carbon source.

The tissue section is not particularly limited. Specifically, it is preferably at least one selected from the group consisting of leaves, stems, roots, buds, petals, cotyledons, hypocotyls, anthers, and seeds, with leaves and stems being preferred among these.

Tissue containing a small amount of latex, and specifically petals, anthers, and seeds, are also preferred.

In the induction step, first, the surfaces of tissue sections of a plant are washed. If the tissue sections are tissue inside of the plant body, the tissue sections may, for example, be cleansed with a cleanser, or may be washed with water containing about 0.1% of a surfactant. If leaves or the like are used, the surfaces are preferably washed using a soft sponge.

Next, the tissue sections are disinfected or sterilized. Disinfection and sterilization may be carried out using well-known disinfectants and sterilants, respectively. Preferred are ethanol, benzalkonium chloride, and aqueous sodium hypochlorite.

Then, the disinfected or sterilized tissue sections are cultured in an induction medium that contains a plant growth hormone and a carbon source to induce calli. Although the induction medium may be liquid or solid, solid culture is preferred because if the tissue sections are placed on the medium and then cultured, then calli can be easily formed. In the case where the induction medium is a liquid medium, static culture or shake culture may be performed.

The plant growth hormone may, for example, be an auxin plant hormone and/or a cytokinin plant hormone.

Examples of the auxin plant hormones include 2,4-dichlorophenoxyacetic acid, naphthaleneacetic acid, indolebutyric acid, indoleacetic acid, indolepropionic acid, chlorophenoxyacetic acid, naphthoxyacetic acid, phenylacetic acid, 2,4,5-trichlorophenoxyacetic acid, parachlorophenoxyacetic acid, 2-methyl-4-chlorophenoxyacetic acid, 4-fluorophenoxyacetic acid, 2-methoxy-3,6-dichlorobenzoic acid, 2-phenyl acid, picloram, and picolinic acid. Preferred among these are 2,4-dichlorophenoxyacetic acid, naphthaleneacetic acid, and indolebutyric acid, with 2,4-dichlorophenoxyacetic acid and naphthaleneacetic acid being more preferred. In the case of using a plant of the family Asteraceae (preferably a plant of the genus *Sonchus*, and especially *Sonchus oleraceus*), naphthaleneacetic acid is still more preferred. In the case of using a plant of the family Euphorbiaceae (preferably a plant of the genus *Hevea*, and especially *Hevea brasiliensis*), 2,4-dichlorophenoxyacetic acid is still more preferred.

Examples of the cytokinin plant hormones include benzyladenine, kinetin, zeatin, benzylaminopurine, isopentynyl aminopurine, thidiazuron, isopentenyladenine, zeatin riboside, and dihydrozeatin. Preferred among these are benzyladenine, kinetin, and zeatin, with benzyladenine and kinetin being more preferred. In the case of using a plant of the family Asteraceae (preferably a plant of the genus *Sonchus*, and especially *Sonchus oleraceus*), benzyladenine is still more preferred. In the case of using a plant of the family Euphorbiaceae (preferably a plant of the genus *Hevea*, and especially *Hevea brasiliensis*), kinetin is still more preferred.

The carbon source is not particularly limited, and examples thereof include sugars such as sucrose, glucose, trehalose, fructose, lactose, galactose, xylose, allose, talose, gulose, altrose, mannose, idose, arabinose, apiose, and maltose. Sucrose and glucose are preferred among these, and sucrose is more preferred.

The induction medium may be a basal medium supplemented with the plant growth hormone, and examples of the basal media include basal media such as White's medium (as disclosed in "Shokubutsu Saibou Kogaku Nyumon", Gakkai Shuppan Center, pp. 20-36), Heller's medium (Heller R, Bot. Biol. Veg., Paris, 14, 1-223 (1953)), S H medium (Schenk and Hildebrandt medium), M S medium (Murashige and Skoog medium) (as disclosed in "Shokubutsu Saibou Kogaku Nyumon", Gakkai Shuppan Center, pp. 20-36), LS medium (Linsmaier and Skoog medium) (as disclosed in "Shokubutsu Saibou Kogaku Nyumon", Gakkai Shuppan Center, pp. 20-36), Gamborg medium, B5 medium (as disclosed in "Shokubutsu Saibou Kogaku Nyumon", Gakkai Shuppan Center, pp. 20-36), MB medium, and WP medium (Woody Plant: for woody plants), as well as modified basal media obtained by modifying the composition of these basal media. Preferred among these are MS, B5, and WP media supplemented with the plant growth hormone. Moreover, the medium preferably contains an auxin plant hormone and a cytokinin plant hormone because such a medium is suitable for callus maintenance and promotion of cell division.

If the induction medium is a solid medium, the medium may be solidified using a solidifying agent. The solidifying agent is not particularly limited, and examples thereof include agar, gellan gum, agarose, gelrite, gelatin, silica gel, agar, and phytagel.

Depending on the type of plant and on whether the medium is a liquid medium or a solid medium, the suitable composition and culture conditions of the induction medium are usually as follows (particularly in the case of using a plant of the family Asteraceae (preferably a plant of the genus *Sonchus*, and especially *Sonchus oleraceus*) or a plant of the family Euphorbiaceae (preferably a plant of the genus *Hevea*, and especially *Hevea brasiliensis*)).

The carbon source concentration in the induction medium is preferably 0.1% by mass or higher, and more preferably 1% by mass or higher. The carbon source concentration is preferably 10% by mass or lower, more preferably 6% by mass or lower, and still more preferably 3% by mass or lower. The carbon source concentration herein means the concentration of sugars.

The auxin plant hormone concentration in the induction medium is preferably 0 mg/L or higher, more preferably $1 \times 10^{-3}$ mg/L or higher, still more preferably 0.05 mg/L or higher, and particularly preferably 0.5 mg/L or higher. In the case of using a plant of the family Euphorbiaceae (preferably a plant of the genus *Hevea*, and especially *Hevea brasiliensis*), the concentration is most preferably 1.5 mg/L or higher. The auxin plant hormone concentration is preferably 20 mg/L or lower, more preferably 10 mg/L or lower, and still more preferably 2.5 mg/L or lower.

The cytokinin plant hormone concentration in the induction medium is preferably 0 mg/L or higher, more preferably $1 \times 10^{-3}$ mg/L or higher, still more preferably 0.1 mg/L or higher, and particularly preferably 0.5 mg/L or higher. In the case of using a plant of the family Euphorbiaceae (preferably a plant of the genus *Hevea*, and especially *Hevea brasiliensis*), the concentration is most preferably 0.8 mg/L or higher. The cytokinin plant hormone concentration is preferably 15 mg/L or lower, more preferably 10 mg/L or lower, still more preferably 3 mg/L or lower, particularly preferably 1.5 mg/L or lower, and most preferably 1.2 mg/L or lower.

The pH of the induction medium is preferably 4.0 to 10.0, more preferably 5.6 to 6.5, and still more preferably 5.7 to 5.8. The culture temperature is preferably 0° C. to 40° C., and more preferably 20° C. to 30° C. In the case of using a plant of the family Asteraceae (preferably a plant of the genus *Sonchus*, and especially *Sonchus oleraceus*), the culture temperature is still more preferably 20° C. to 26° C. Although culture may be carried out in a dark place or a bright place, the illuminance is preferably 0 to 100000 lx, and more preferably 2000 to 25000 lx. The culture time is not particularly limited, and culture is preferably carried out for 1 to 10 weeks.

The pH of a solid medium herein means the pH of a medium supplemented with all the components excluding solidifying agent. The dark place herein means that the illuminance is 0 to 0.1 lx, and the bright place herein means that the illuminance is more than 0.1 lx.

The solidifying agent concentration in the induction medium which is a solid medium is preferably 0.1% by mass or higher, and more preferably 0.2% by mass or higher. The solidifying agent concentration is preferably 2% by mass or lower, more preferably 1.1% by mass or lower, and still more preferably 0.6% by mass or lower.

In particular, in the case of using a plant of the family Asteraceae (preferably a plant of the genus *Sonchus*, and especially *Sonchus oleraceus*), among the above conditions particularly preferred are as follows: the auxin plant hormone is naphthaleneacetic acid at a concentration of 0.5 to 2.5 mg/L, the cytokinin plant hormone is benzyladenine and the culture temperature is 20° C. to 26° C.

In particular, in the case of using a plant of the family Euphorbiaceae (preferably a plant of the genus *Hevea*, and especially *Hevea brasiliensis*), among the above conditions particularly preferred are as follows: the auxin plant hormone is 2,4-dichlorophenoxyacetic acid at a concentration of 1.5 to 2.5 mg/L, and the cytokinin plant hormone is kinetin at a concentration of 0.8 to 1.2 mg/L.

As described above, calli can be induced by culturing the disinfected or sterilized tissue sections in the induction medium.

In the present invention, the induced calli may be genetically modified. Recombinant genes may be introduced by common methods in generally known conditions. Non-limiting examples include protoplast method, particle gun method, and *agrobacterium* method (all as disclosed in "Seibutu Kagaku Jikkenhou 41, Shokubutsu Saibou Kogaku Nyumon", Sep. 1, 1998, Gakkai Shuppan Center, pp. 255-326, and "Plant Biotechnology", May 25, 2009, Saiwai Shobo, pp. 130-136).

The induced calli may be directly used in the regeneration induction step. It is preferred that the induced callus be first reproduced and then used in the regeneration induction step because then plants can be reproduced in larger quantities. The callus may be reproduced by culturing the calli in conditions capable of reproducing the callus. For example, the callus can be reproduced by culturing the calli in a medium having the same composition in the same culture conditions as in the induction step.

(Regeneration Induction Step)

In the regeneration induction step, the calli are cultured in a regeneration induction medium that contains a plant growth hormone and a carbon source to form adventitious embryos and shoots. By inducing (forming) adventitious embryos from the calli, followed by culturing the adventitious embryos, shoots can be stably formed. Thus, the culture conditions in the regeneration induction step may be any conditions capable of inducing adventitious embryos from calli.

In the regeneration induction step, adventitious embryos are induced, for example, by culturing the calli induced in the induction step in the regeneration induction medium (the calli may be one genetically modified by the above method, or one obtained by reproduction of the calli induced in the induction step). Although the regeneration induction medium may be liquid or solid, solid culture is preferred because if the calli are placed on the medium and then cultured, then adventitious embryos can be easily induced. In the case where the regeneration induction medium is a liquid medium, static culture or shake culture may be performed.

The regeneration induction medium may be a basal medium supplemented with the plant growth hormone, and examples of the basal media include the basal media mentioned above, and modified basal media obtained by modifying the composition of the basal media. MS, LS, B5, and WP media supplemented with the plant growth hormone are preferred among these, and an MS medium supplemented with the plant growth hormone is more preferred. The plant growth hormone and the carbon source may suitably be as mentioned for the induction medium. The medium preferably contains an auxin plant hormone and a cytokinin plant hormone, and more preferably contains naphthaleneacetic acid and benzyladenine, because such media are suitable for adventitious embryo induction.

If the regeneration induction medium is a solid medium, the medium may be solidified using a solidifying agent as in the case of the induction medium.

Depending on the type of plant and on whether the medium is a liquid medium or a solid medium, the suitable composition and culture conditions of the regeneration induction medium are usually as follows (particularly in the case of using a plant of the family Asteraceae (preferably a plant of the genus *Sonchus*, and especially *Sonchus oleraceus*) or a plant of the family Euphorbiaceae (preferably a plant of the genus *Hevea*, and especially *Hevea brasiliensis*)).

The carbon source concentration in the regeneration induction medium is preferably 0.1% by mass or higher, more preferably 1% by mass or higher, and still more preferably 2% by mass or higher. The carbon source concentration is preferably 10% by mass or lower, more preferably 6% by mass or lower, and still more preferably 5% by mass or lower. In the case of using a plant of the family Asteraceae (preferably a plant of the genus *Sonchus*, and especially *Sonchus oleraceus*), the concentration is particularly preferably 4% by mass or lower.

The auxin plant hormone concentration in the regeneration induction medium is preferably 0 mg/L or higher, more preferably $1 \times 10^{-3}$ mg/L or higher, still more preferably $5 \times 10^{-3}$ mg/L or higher, and particularly preferably 0.01 mg/L or higher. In the case of using a plant of the family Euphorbiaceae (preferably a plant of the genus *Hevea*, and especially *Hevea brasiliensis*), the concentration is most preferably 0.03 mg/L or higher. The auxin plant hormone concentration is preferably 15 mg/L or lower, more preferably 8 mg/L or lower, still more preferably 5 mg/L or lower, particularly preferably 1 mg/L or lower, most preferably 0.5 mg/L or lower, and even most preferably 0.1 mg/L or lower. In the case of using a plant of the family Asteraceae (preferably a plant of the genus *Sonchus*, and especially *Sonchus oleraceus*), the concentration is yet even most preferably 0.03 mg/L or lower.

The cytokinin plant hormone concentration in the regeneration induction medium is preferably 0 mg/L or higher, more preferably $1 \times 10^{-3}$ mg/L or higher, still more preferably 0.01 mg/L or higher, particularly preferably 0.5 mg/L or higher, and most preferably 0.8 mg/L or higher. The cytokinin plant hormone concentration is preferably 15 mg/L or lower, more preferably 10 mg/L or lower, still more preferably 5 mg/L or lower, particularly preferably 2 mg/L or lower, most preferably 1.5 mg/L or lower, and even most preferably 1.2 mg/L or lower. When the cytokinin plant hormone concentration falls within the range mentioned above, particularly adventitious embryos can be suitably induced and shoots can be suitably formed.

The regeneration induction medium may be supplemented with FeNaEDTA for preventing accumulation of tissue growth inhibitors. The regeneration induction medium may also be supplemented with gibberellin for accelerating the formation of adventitious embryos.

The pH of the regeneration induction medium is not particularly limited, and is preferably 4.0 to 10.0, and more preferably 5.6 to 6.5. The culture temperature is preferably 0° C. to 40° C., more preferably 20° C. to 36° C., and still more preferably 23° C. to 32° C. Although culture may be carried out in a dark place or a bright place, culture is preferably carried out in a bright place where the illuminance is preferably 2000 to 25000 lx for 10 to 16 hours per 24 hours. The culture time is not particularly limited, and culture is preferably carried out for 5 to 48 weeks, more preferably 5 to 24 weeks. In the case of using a plant of the family Asteraceae (preferably a plant of the genus *Sonchus*, and especially *Sonchus oleraceus*), culture is still more preferably carried out for 5 to 10 weeks. In the case of using a plant of the family Euphorbiaceae (preferably a plant of the genus *Hevea*, and especially *Hevea brasiliensis*), culture is particularly preferably carried out for 16 to 48 weeks.

The solidifying agent concentration in the regeneration induction medium which is a solid medium is preferably 0.1% by mass or higher, and more preferably 0.15% by mass or higher. The solidifying agent concentration is preferably 2% by mass or lower, more preferably 1.1% by mass or lower, still more preferably 0.6% by mass or lower, and particularly preferably 0.3% by mass or lower.

In the case of using a plant of the family Asteraceae (preferably a plant of the genus *Sonchus*, and especially *Sonchus oleraceus*), it is preferred that the regeneration induction medium contain an MS basal medium and further contain sucrose at a concentration of 2 to 4% by mass, naphthaleneacetic acid at a concentration of $1 \times 10^{-3}$ to 0.03 mg/L, benzyladenine at a concentration of 0.8 to 1.2 mg/L, and a solidifying agent (gellan gum) at a concentration of 0.1 to 0.3% by mass.

In the case of using a plant of the family Euphorbiaceae (preferably a plant of the genus *Hevea*, and especially *Hevea brasiliensis*), it is preferred that the regeneration induction medium contain an MS basal medium and further contain naphthaleneacetic acid at a concentration of 0.03 to 0.5 mg/L, benzyladenine at a concentration of 0.01 to 1.2 mg/L, and a solidifying agent (gellan gum) at a concentration of 0.1 to 0.6% by mass.

As described above, in the regeneration induction step, adventitious embryos and shoots can be formed by culturing the calli in the regeneration induction medium. The shoots formed in the regeneration induction step are used in the subsequent elongation step. The preferred timing for the subsequent elongation step is when shoots have been visually observed and their stable growth has then been confirmed. The subsequent elongation step may be skipped so that the shoots formed in the regeneration induction step can be directly used in the rooting step. The regeneration induction step corresponds to the method of inducing adventitious embryos of the present invention.

(Elongation Step)

In the elongation step, the formed shoots are cultured in an elongation medium to elongate the shoots.

In the elongation step, the shoots are elongated, for example, by culturing the shoots formed in the regeneration induction step in an elongation medium. Although the elongation medium may be liquid or solid, solid culture is preferred because if the shoots are placed on the medium and then cultured, then the shoots can be easily elongated. In the case where the elongation medium is a liquid medium, static culture or shake culture may be performed.

The elongation medium may be any of the basal media mentioned above, and modified basal media obtained by modifying the composition of the basal media. Particularly in the case of using a plant of the family Asteraceae (preferably a plant of the genus *Sonchus*, and especially *Sonchus oleraceus*), the elongation medium is preferably a medium free of plant growth hormones, and more preferably an MS medium free of plant growth hormones, because such a medium allows the shoots to be suitably elongated. The carbon source may suitably be as mentioned for the induction medium.

If the elongation medium is a solid medium, the medium may be solidified using a solidifying agent as in the case of the induction medium.

Depending on the type of plant and on whether the medium is a liquid medium or a solid medium, the suitable culture conditions in the elongation step are usually as follows (particularly in the case of using a plant of the family Asteraceae (preferably a plant of the genus *Sonchus*, and especially *Sonchus oleraceus*) or a plant of the family Euphorbiaceae (preferably a plant of the genus *Hevea*, and especially *Hevea brasiliensis*)).

The pH of the elongation medium is not particularly limited, and is preferably 4.0 to 10.0, and more preferably 5.6 to 6.5. The culture temperature is preferably 0° C. to 40° C., more preferably 20° C. to 36° C., and still more preferably 20° C. to 30° C. Although culture may be carried out in a dark place or a bright place, culture is preferably carried out in a bright place where the illuminance is preferably 2000 to 25000 lx for 10 to 16 hours per 24 hours. The culture time is not particularly limited, and culture is preferably carried out for 5 to 10 weeks.

The solidifying agent concentration in the elongation medium which is a solid medium is preferably 0.1% by mass or higher, and more preferably 0.2% by mass or higher. The solidifying agent concentration is preferably 2% by mass or lower, more preferably 1.1% by mass or lower, and still more preferably 0.6% by mass or lower.

As described above, in the elongation step, the formed shoots can be elongated by culturing the shoots in the elongation medium. In the elongation step, the shoots are not only elongated, but new shoots are also formed. The shoots elongated in the elongation step are used in the subsequent rooting step. The preferred timing for the subsequent rooting step is when the shoots have been elongated to about 2 to 3 cm.

(Rooting Step)

In the rooting step, the shoots are cultured in a rooting medium to root the shoots. The shoots used may be the shoots elongated in the elongation step, or the shoots formed in the regeneration induction step may be directly used in this step.

In the rooting step, the shoots are rooted, for example, by culturing the shoots elongated in the elongation step or the shoots formed in the regeneration induction step in a rooting medium. Although the rooting medium may be liquid or solid, solid culture is preferred because if the shoots are placed on the medium and then cultured, then the shoots can be easily rooted. In the case where the rooting medium is a liquid medium, static culture or shake culture may be performed.

The rooting medium may be any of the basal media mentioned above, and modified basal media obtained by modifying the composition of the basal media. The rooting medium is preferably a medium free of plant growth hormones because such a medium allows the shoots to be suitably rooted. In the case of using a plant of the family Asteraceae (preferably a plant of the genus *Sonchus*, and especially *Sonchus oleraceus*), the rooting medium is more preferably a B5 medium free of plant growth hormones. In the case of using a plant of the family Euphorbiaceae (preferably a plant of the genus *Hevea*, and especially *Hevea brasiliensis*), the rooting medium is more preferably a 1/2 MS medium which may or may not contain a plant growth hormone. Moreover, the carbon source may suitably be as mentioned for the induction medium. The composition of the rooting medium may be the same as that of the elongation medium. Moreover, if the shoots have already been rooted in the elongation step, the rooting step may be skipped.

If the rooting medium is a solid medium, the medium may be solidified using a solidifying agent as in the case of the induction medium.

Depending on the type of plant and on whether the medium is a liquid medium or a solid medium, the suitable culture conditions in the rooting step are usually as follows (particularly in the case of using a plant of the family Asteraceae (preferably a plant of the genus *Sonchus*, and especially *Sonchus oleraceus*) or a plant of the family Euphorbiaceae (preferably a plant of the genus *Hevea*, and especially *Hevea brasiliensis*)).

The pH of the rooting medium is not particularly limited, and is preferably 4.0 to 10.0, and more preferably 5.6 to 6.5. The culture temperature is preferably 0° C. to 40° C., more preferably 10° C. to 36° C., and still more preferably 20° C. to 30° C. In the case of using a plant of the family Asteraceae (preferably a plant of the genus *Sonchus*, and especially *Sonchus oleraceus*), the culture temperature is particularly preferably 20° C. to 25° C. In the case of using a plant of the family Euphorbiaceae (preferably a plant of the genus *Hevea*, and especially *Hevea brasiliensis*) the culture temperature is particularly preferably 25° C. to 32° C.

Although culture may be carried out in a dark place or a bright place, culture is preferably carried out in a bright place where the illuminance is preferably 2000 to 25000 lx for 10 to 16 hours per 24 hours. The culture time is not particularly limited, and culture is preferably carried out for 4 to 10 weeks.

The solidifying agent concentration in the rooting medium which is a solid medium is preferably 0.1% by mass or higher, more preferably 0.2% by mass or higher, and still more preferably 0.3% by mass or higher. The solidifying agent concentration is preferably 2% by mass or lower, more preferably 1.1% by mass or lower, and still more preferably 0.6% by mass or lower.

As described above, in the rooting step, the elongated shoots can be rooted by culturing the shoots in the rooting medium. Thus rooted shoots (juvenile plants) are obtained. The juvenile plants may be directly transplanted in the soil. Preferably, the juvenile plants are transferred to and acclimatized in an artificial soil such as vermiculite before they are transplanted in the soil.

As described above, in the present invention, adventitious embryos can be induced from calli, the adventitious embryos can be cultured to stably form shoots, and the formed shoots can be elongated and rooted, whereby calli can be stably regenerated into plants. Further, by tissue culture under a controlled environment, plants can be stably reproduced without being affected by weather, seasons or other factors.

EXAMPLES

Hereinafter, the present invention will be described in more detail by reference to examples which are not intended to limit the scope of the present invention.

The following is the list of the chemicals used in the examples using *Sonchus oleraceus*.
NAA: naphthaleneacetic acid
BA: benzyladenine
*Sonchus oleraceus*: plants aseptically germinated from seeds of *Sonchus oleraceus* naturally grown in Nada ward, Kobe, Japan.

(Callus Induction (Induction Step))

Leaves and stems were collected from *Sonchus oleraceus*. Then the surfaces of the collected leaves and stems were washed with running water and further washed with 70% ethanol. Subsequently, they were sterilized with a solution of sodium hypochlorite diluted to about 5 to 10% and then washed with running water again.

Next, tissue sections of the sterilized leaves and stems were inserted in an induction medium (solid medium) and cultured (induction step). The induction medium was prepared by supplementing MS medium (as disclosed in "Shokubutsu Saibou Kogaku Nyumon", Gakkai Shuppan Center, pp. 20-36) with naphthaleneacetic acid (NAA, 1.0 mg/L), benzyladenine (BA, 0.1 mg/L), and sucrose (3% by mass), adjusting the pH of the medium to 5.7 to 5.8, and then adding gellan gum at 0.2% by mass to the medium, followed by sterilization in an autoclave (121° C., 20 minutes) and then cooling in a clean bench.

The tissue sections of *Sonchus oleraceus* were inserted in the induction medium (solid medium) and cultured at 23° C. for four weeks in a bright place (10000 lx). Thus, calli (undifferentiated cells) was induced from the tissue sections of *Sonchus oleraceus*.

(Study of Medium for Forming Adventitious Embryos and Shoots (Regeneration Induction Step))

Next, conditions of the medium (regeneration induction medium) for forming adventitious embryos and shoots from the induced calli were studied using MS basal medium. Specifically, MS media supplemented with NAA (an auxin plant hormone), BA (a cytokinin plant hormone), and sucrose (a sugar) at various concentrations were used for the study (see Table 1). The pH was adjusted to 5.7 to 5.8. To the media was added gellan gum as a solidifying agent at 0.2% by mass. Then, the calli induced in the induction step were cultured in the prepared solid media. (sterilized) at 23° C. with a light cycle of 12 hours light (10000 lx) per 24 hours for eight weeks. Table 1 shows the rates of adventitious embryo formation after the eight weeks' culture. In the media where adventitious embryos were formed, shoot formation was also observed after the adventitious embryo formation. In contrast, in the media where no adventitious embryos were formed, no shoots were formed either. This demonstrated that by inducing adventitious embryos from calli, shoots can be stably formed.

The rates of adventitious embryo formation were calculated by dividing the number of calli showing adventitious embryo formation by the number of calli transplanted in the regeneration induction medium.

(Shoot Elongation (Elongation Step))

Next, for shoot elongation, the formed shoots were transplanted in an MS medium free of plant growth hormones. The pH of the medium was adjusted to 5.7. The shoots were cultured in the 0.4% gellan gum-containing solid medium (sterilized) at 23° C. with a light cycle of 12 hours light (10000 lx) per 24 hours for eight weeks. By culture in the medium free of plant growth hormones, good shoot elongation was observed. Table 1 shows the results.

(Rooting (Rooting Step))

Next, for rooting, the shoots grown to about 3 cm were transplanted in a B5 medium free of plant growth hormones. The pH of the medium was adjusted to 5.8. The shoots were cultured in the 0.4% gellan gum-containing solid medium (sterilized) at 23° C. with a light cycle of 12 hours light (10000 lx) per 24 hours for eight weeks. By culture in the medium free of plant growth hormones, good rooting was observed. Table 1 shows the results.

In Table 1, elongation and rooting of shoots were evaluated according to the following criteria.
Good: Not less than 10% of shoots were elongated/rooted.
Acceptable: Less than 10% of shoots were elongated/rooted.
Poor: No shoots were elongated.

TABLE 1

| No. | Temperature (° C.) | NAA concentration (mg/L) | BA concentration (mg/L) | Sucrose concentration (% by mass) | Rate of adventitious embryo formation (%) | Shoot elongation after transplantation |
| --- | --- | --- | --- | --- | --- | --- |
| 1 | 23 | 5 | 0.05 | 5 | 1 | Acceptable |
| 2 | 23 | 5 | 0.01 | 3 | 0 | Poor |
| 3 | 23 | 5 | 0 | 1 | 1 | Acceptable |
| 4 | 23 | 3 | 0.05 | 5 | 0 | Poor |
| 5 | 23 | 3 | 0.01 | 3 | 0 | Poor |
| 6 | 23 | 3 | 0 | 1 | 1 | Acceptable |
| 7 | 23 | 1 | 0.05 | 1 | 0 | Poor |
| 8 | 23 | 1 | 0.01 | 3 | 3 | Acceptable |
| 9 | 23 | 1 | 0 | 5 | 5 | Acceptable |

TABLE 1-continued

| No. | Temperature (° C.) | NAA concentration (mg/L) | BA concentration (mg/L) | Sucrose concentration (% by mass) | Rate of adventitious embryo formation (%) | Shoot elongation after transplantation |
|---|---|---|---|---|---|---|
| 10 | 23 | 0.05 | 5 | 3 | 0 | Poor |
| 11 | 23 | 0.05 | 3 | 2 | 1 | Acceptable |
| 12 | 23 | 0.05 | 1 | 3 | 10 | Good |
| 13 | 23 | 0.01 | 5 | 3 | 0 | Poor |
| 14 | 23 | 0.01 | 3 | 3 | 1 | Acceptable |
| 15 | 23 | 0.01 | 1 | 3 | 15 | Good |
| 16 | 23 | 0 | 5 | 3 | 0 | Poor |
| 17 | 23 | 0 | 3 | 3 | 0 | Poor |
| 18 | 23 | 0 | 1 | 5 | 0 | Poor |

The results of Table 1 indicate that, in the regeneration induction step, when the rate of adventitious embryo formation was high, the subsequent formation, elongation, and rooting of shoots stably proceeded. This demonstrated that by inducing adventitious embryos from calli, shoots can then be stably formed and the formed shoots can be elongated and rooted, whereby plants can be stably regenerated from calli, and therefore plants can be stably reproduced.

The following is the list of the chemicals used in the examples using *Hevea brasiliensis*.

NAA: naphthaleneacetic acid 2,4-D: 2,4-dichlorophenoxyacetic acid

IBA: indolebutyric acid

BA: benzyladenine

KI: kinetin

Gelling agent: Gelrite, gellan gum

*Hevea brasiliensis*: obtained from Arboricultural Research Institute, Kagaku no Mori Kyoiku Kenkyu Center, Graduate School of Agricultural and Life Sciences, the University of Tokyo (Callus Induction (Induction Step))

Leaves were collected from *Hevea brasiliensis*. Then the surfaces of the collected leaves were washed with running water and further washed with 70% ethanol. Subsequently, they were sterilized with a solution of sodium hypochlorite diluted to about 5 to 10% and then washed with running water again.

Next, the tissue sections of the sterilized leaves were inserted in an induction medium (solid medium) and cultured (induction step). The induction medium was prepared by supplementing MS medium (as disclosed in "Shokubutsu Saibou Kogaku Nyumon", Gakkai Shuppan Center, pp. 20-36) with 2,4-dichlorophenoxyacetic acid (2,4-D, 2.0 mg/L), kinetin (KI, 1.0 mg/L), and sucrose (3% by mass), adjusting the pH of the medium to 5.7 to 5.8, and then adding gellan gum at 0.2% by mass to the medium, followed by sterilization in an autoclave (121° C., 20 minutes) and then cooling in a clean bench.

The tissue sections of *Hevea brasiliensis* were inserted in the induction medium (solid medium) and cultured at 25° C. in a dark place for eight weeks. Thus, calli (undifferentiated cells) were induced from the tissue sections of *Hevea brasiliensis*.

Study of Medium for Forming Adventitious Embryos and Shoots (Regeneration Induction Step))

Next, conditions of the medium (regeneration induction medium) for forming adventitious embryos and shoots from the induced calli were studied using MS basal medium. Specifically, MS media supplemented with NAA (an auxin plant hormone), BA (a cytokinin plant hormone), and sucrose (a sugar) at various concentrations, and optionally further supplemented with FeNaEDTA and gibberellin, were used for the study (see Table 2). The pH was adjusted to 5.7 to 5.8. To the media was added gellan gum as a solidifying agent at 0.4% by mass. Then, the calli induced in the induction step were cultured in the prepared solid media (sterilized) at 25° C. with a light cycle of 12 hours light (10000 lx) per 24 hours for 3 to 6 months. The media were renewed every month during the culture. Table 2 shows the rates of adventitious embryo formation after the 3 to 6 months' culture. In the media where adventitious embryos were formed, shoot formation was also observed after the adventitious embryo formation. In contrast, in the media where no adventitious embryos were formed, no shoots were formed either. This demonstrated that by inducing adventitious embryos from calli, shoots can be stably formed.

The rates of adventitious embryo formation were calculated by dividing the number of calli showing adventitious embryo formation by the number of calli transplanted in the regeneration induction medium.

(Shoot Elongation (Elongation Step))

Next, for shoot elongation, the formed shoots were subcultured in a medium having the same composition as that of the regeneration induction medium. The shoots were cultured at 25° C. with a light cycle of 12 hours light (10000 lx) per 24 hours for eight weeks. Good shoot elongation was observed. Table 2 shows the results.

(Rooting (Rooting Step))

Next, for rooting, the shoots grown to about 3 cm were transplanted in a ½MS medium free of plant growth hormones or a ½MS medium containing a plant growth hormone. The pH of the media was adjusted to 5.7. The shoots were cultured in the 0.4% gellan gum-containing solid media (sterilized) at 25° C. with a light cycle of 12 hours light (10000 lx) per 24 hours for eight weeks. By culture in each of the media, good rooting was observed. Table 2 shows the results.

In Table 2, elongation and rooting of shoots were evaluated according to the following criteria.

Good: Not less than 10% of shoots were elongated/rooted.

Acceptable: Less than 10% of shoots were elongated/rooted.

Poor: No shoots were elongated.

TABLE 2

| No. | Temperature (°C.) | NAA concentration (mg/L) | BA concentration (mg/L) | Sucrose concentration (% by mass) | FeNaEDTA concentration (mg/L) | Gibberellin | Rate of adventitious embryo formation (%) | Shoot elongation after transplantation |
|---|---|---|---|---|---|---|---|---|
| 1 | 25 | 0.02 | 0.01 | 5 | — | — | 1 | Acceptable |
| 2 | 25 | 0.06 | 0.03 | 5 | — | — | 30 | Good |
| 3 | 25 | 0.6 | 0.03 | 5 | — | — | 2 | Acceptable |
| 4 | 25 | 0.6 | 0.5 | 5 | — | — | 0 | Poor |
| 5 | 25 | 1.0 | 0.5 | 5 | — | — | 25 | Good |
| 6 | 25 | 1.0 | 1.0 | 5 | — | — | 0 | Poor |
| 7 | 25 | 1.0 | 2.0 | 5 | — | — | 0 | Poor |
| 8 | 25 | 0.1 | 2.0 | 5 | 55 | 1.0 | 7 | Acceptable |
| 9 | 25 | 0.1 | 4.0 | 5 | 55 | 0.2 | 5 | Acceptable |
| 10 | 25 | 2.0 | 2.0 | 5 | — | — | 0 | Poor |
| 11 | 25 | 0.02 | 4.0 | 5 | 55 | — | 0 | Poor |
| 12 | 25 | 0 | 6.0 | 5 | — | — | 0 | Poor |
| 13 | 25 | 0 | 0 | 5 | — | — | 0 | Poor |

The results of Table 2 indicate that, in the regeneration induction step, when the rate of adventitious embryo formation was high, the subsequent formation, elongation, and rooting of shoots stably proceeded. This demonstrated that by inducing adventitious embryos from calli, shoots can then be stably formed and the formed shoots can be elongated and rooted, whereby plants can be stably regenerated from calli, and therefore plants can be stably reproduced.

The invention claimed is:

1. A method of regenerating a plant, comprising: a step of inducing adventitious embryos from calli in a regeneration induction medium that contains naphthaleneacetic acid and benzyladenine, wherein said plant is a plant of the genus *Sonchus*, and wherein a concentration of the naphthaleneacetic acid is $1 \times 10^{-2}$ to 0.05 mg/L, and a concentration of the benzyladenine is 0.8 to 1.2 mg/L.

2. The method of regenerating the plant according to claim 1,
wherein the adventitious embryo induction is followed by forming shoots.

3. The method of regenerating the plant according to claim 1, comprising:
a regeneration induction step of culturing the calli in a regeneration induction medium that contains naphthaleneacetic acid, benzyladenine, and a carbon source to form the adventitious embryos and shoots; and
a rooting step of culturing the shoots in a rooting medium to root the shoots.

4. The method of regenerating the plant according to claim 1, comprising:
a regeneration induction step of culturing the calli in a regeneration induction medium that contains naphthaleneacetic acid, benzyladenine, and a carbon source to form the adventitious embryos and shoots;
an elongation step of culturing the formed shoots in an elongation medium to elongate the shoots; and
a rooting step of culturing the elongated shoots in a rooting medium to root the shoots.

5. The method of regenerating the plant according to claim 4,
wherein the elongation medium and the rooting medium are free of plant growth hormones.

6. The method of regenerating the plant according to claim 1,
wherein the plant is *Sonchus oleraceus*.

7. A method of reproducing a plant, comprising: a step of inducing adventitious embryos from calli in a regeneration induction medium that contains naphthaleneacetic acid and benzyladenine, wherein said plant is plant of the genus *Sonchus*, and wherein a concentration of the naphthaleneacetic acid is $1 \times 10^{-2}$ to 0.05 mg/L, and a concentration of the benzyladenine is 0.8 to 1.2 mg/L.

8. The method of reproducing the plant according to claim 7, comprising a step of inducing the calli from tissue sections of the plant.

9. The method of reproducing the plant according to claim 7,
wherein the adventitious embryo induction is followed by forming shoots.

10. The method of reproducing the plant according to claim 7, comprising:
an induction step of culturing tissue sections of the plant in an induction medium that contains a plant growth hormone and a carbon source to induce the calli;
a regeneration induction step of culturing the calli in a regeneration induction medium that contains naphthaleneacetic acid, benzyladenine, and a carbon source to form the adventitious embryos and shoots; and
a rooting step of culturing the shoots in a rooting medium to root the shoots.

11. The method of reproducing the plant according to claim 7, comprising:
an induction step of culturing tissue sections of the plant in an induction medium that contains a plant growth hormone and a carbon source to induce the calli;
a regeneration induction step of culturing the calli in a regeneration induction medium that contains naphthaleneacetic acid, benzyladenine, and a carbon source to form the adventitious embryos and shoots;
an elongation step of culturing the formed shoots in an elongation medium to elongate the shoots; and
a rooting step of culturing the elongated shoots in a rooting medium to root the shoots.

12. The method of plant according to claim 7,
wherein the plant is *Sonchus oleraceus*.

13. A method of inducing adventitious embryos of a plant of the genus *Sonchus*, comprising: culturing calli a medium that contains naphthaleneacetic acid, benzyladenine, and a carbon source to induce the adventitious embryos, wherein the medium has a concentration of the naphthaleneacetic acid of $1 \times 10^{-2}$ to 0.05 mg/L, and a concentration of the benzyladenine of 0.8 to 1.2 mg/L.

14. The method of inducing adventitious embryos according to claim 13, wherein the medium has a solidifying agent concentration of 0.1 to 2% by mass.

* * * * *